(12) United States Patent
Borodulin et al.

(10) Patent No.: US 6,379,299 B1
(45) Date of Patent: Apr. 30, 2002

(54) VAGINAL SPECULUM WITH ADJUSTABLE BLADES

(76) Inventors: German Borodulin, 583 46th Ave., San Francisco, CA (US) 94121; Ananias Diokno, 480 Hillspur Rd., Ann Arbor, MI (US) 48105; Alexander Shkolnik, 485 Dartmouth Ave., San Carlos, CA (US) 94070

( * ) Notice: Subject to any disclaimer, the term of this patent is extended or adjusted under 35 U.S.C. 154(b) by 0 days.

(21) Appl. No.: 09/565,613

(22) Filed: May 4, 2000

(51) Int. Cl.[7] ................................................ A61B 1/32
(52) U.S. Cl. ...................... 600/220; 600/215; 600/222
(58) Field of Search ............................. 600/212, 222, 600/223, 202, 221, 225, 184, 186, 220, 245, 224

(56) References Cited

U.S. PATENT DOCUMENTS 2,483,233 A * 9/1949 Price et al. ................. 600/220
2,579,849 A * 12/1951 Newman ..................... 600/220
3,716,047 A * 2/1973 Moore et al. ................. 128/18
3,747,591 A * 7/1973 Golden ........................ 600/220
3,815,585 A * 6/1974 Fiore .......................... 600/202
4,350,151 A * 9/1982 Scott .......................... 600/225

* cited by examiner

Primary Examiner—Pedro Philogene
(74) Attorney, Agent, or Firm—I. Zborovsky

(57) ABSTRACT

A vaginal speculum consisting of two blades pivotally interconnected through a fork-like member so that the blades can be expanded and fixed in an expanded state in order to dilate the vagina for observing the condition of the vagina cavity. The device is characterized by having adjustable blades, which can be withdrawn partially or completely for replacement with blades of other dimensions without withdrawing the entire speculum from the vagina. In a closed state, the distal ends of the blades form a bifocal lens, which can be used for visually detecting changes, associated with an earlier stage of cancer or erosion. Provision of retractable blades makes it possible for a physician to withdraw the blades in an alternating sequence for exposing one of the walls of the vagina cavity by pressing down with the longer blade on the opposite wall.

31 Claims, 8 Drawing Sheets

VAGINAL SPECULUM WITH ADJUSTABLE BLADES

CROSS-REFERENCES TO RELATED APPLICATIONS

"Not Applicable".

STATEMENT REGARDING FEDERALLY SPONSORED RESEARCH OR DEVELOPMENT

"Not Applicable".

REFERENCE TO "MICROFICHE APPENDIX"

"Not Applicable".

BACKGROUND OF THE INVENTION

1. Field of the Invention

The present invention relates to medical diagnostic instruments, in particular to a vaginal speculum for visual examination of the vaginal cavity, vaginal walls, and conditions of the cervix.

2. Description of the Related Art

A vaginal speculum is a diagnostic instrument for dilating the opening of the vagina cavity in order that the interior may be more easily visible for observation. A vaginal speculum has two expandable blades, which are inserted into the vagina in a closed state and then expanded, or moved apart for dilating the vaginal cavity. In particular, a vaginal speculum is an indispensable instrument not only for gynecologists but also for primary care physicians, geriatricians, urologists, and nurse practitioners for urological examination of patients suffering from urinary incontinence in order to exclude the presence of vaginal prolapses, such as rectocele, cystocele, enterocele, and uterine prolapse. Vaginal prolapses of the aforementioned type are protrusions or herniation of the urethra or other pelvic organs into the vagina.

One typical vaginal speculum is described in U.S. Pat. No. 3,716,047. The instrument consists of three parts of molded non-toxic plastic materials, i.e., a fixed member, a movable member, and a sliding member. The sliding member is slidingly installed in the fixed member and pivotally supports the movable member so that the movable member can be rotated around the pivot at the proximal end of the fixed member. As a result, the distal ends of the movable and fixed members, which form expandable blades insertable into the vagina, can dilate the vagina cavity and thus allow internal vaginal observations. The members are made from a transparent plastic and the blades form a thin-wall circular or oval cross-section, which allows the observation.

A procedure of examination of a vagina with the use of a speculum involves movements of the speculum in an expanded, i.e., an outwardly diverging state in the direction towards or away from the uterus. This is necessary for diagnosing aforementioned vaginal prolapses. However, since the opening of the vagina has a circular muscle, which is more resistant to dilations than the vaginal cavity, the aforementioned withdrawal of the expanded speculum may cause in patient discomfort and painful sensations. This is because in the course of the withdrawal of the speculum the diameter of its portion at the vaginal opening is stretched by the speculum. Furthermore, the conventional vaginal specula do not have features for measuring the length of vagina and for testing and measuring the severity of the prolapses without completely removing the entire speculum.

Normally, the physician disassembles the speculum and inserts only one of the blades for pressing on one wall of the vagina for exposing and observing the opposite wall. In case of prolapses, a separate ruler is used for measuring the length and position of the prolapse or prolapses. The procedure is then repeated for expositing the opposite wall of the vagina cavity. In some cases, the physician uses a separate single metal blade for pressing on the anterior and posterior walls of the vagina cavity. Thus, the examination involves the use of several tools, as well as assembling and disassembling operations. Thus, it is impossible with conventional specula to conduct more concentrated and localized examination of one wall of the vaginal cavity without removing the entire speculum from the vagina.

In examining the conditions of the cervix with the use of known vaginal specula, it is difficult to diagnose cervical papilomas at the initial stage of their development. This is because such initial papilomas are very small. A papiloma is a growth pattern of epithelial tumors.

BRIEF SUMMARY OF THE INVENTION

It is an object of the present invention to provide a disposable vaginal speculum, which is simple in construction, easy to operate, inexpensive to manufacture, allows painless withdrawal of the speculum blades in an expanded state, has adjustable blades, provides means for measuring the length of the vagina, testing for and measuring the severity of the prolapse, provides optical magnification means for enlargement of the observed area, and gives allowance to concentrate the observation separately on each wall of the vagina.

A vaginal speculum consisting of two blades pivotally interconnected through a fork-like member so that the blades can be expanded and fixed in an expanded state in order to dilate the vagina for observing the condition of the vagina cavity. The device is characterized by having moveable blades, which can be withdrawn partially or completely from an axially-fixed main parts and for replacement with blades of other dimensions without withdrawing the entire speculum from the vagina. In a closed state, the distal ends of the blades form a bifocal lens, which can be used for visually detecting changes, associated with an earlier stage of cancer or erosion. Provision of retractable blades makes it possible for a physician to withdraw the blades in an alternating sequence for exposing one of the walls of the vagina cavity by pressing down with the longer blade on the opposite wall.

SUMMARY OF THE INVENTION

A vaginal speculum consisting of two blades pivotally interconnected through a fork-like member so that the blades can be expanded and fixed in an expanded state in order to dilate the vagina for observing the condition of the vagina cavity. The device is characterized by having adjustable blades, which can be withdrawn partially or completely for replacement with blades of other dimensions without withdrawing the entire speculum from the vagina. In a closed state, the distal ends of the blades form a bifocal lens, which can be used for visually detecting changes, associated with an earlier stage of cancer or erosion. Provision of retractable blades makes it possible for a physician to withdraw the blades in an alternating sequence for exposing one of the walls of the vagina cavity by pressing down with the longer blade on the opposite wall.

DETAILED DESCRIPTION OF THE INVENTION

In general, a vaginal speculum of the present invention is similar to the one described in U.S. Pat. No. 3,716,047 and is aimed at its improvement, as well as at an improvement of any other vaginal speculum of the type having two blades which are expanded by rotating around a pivot at their proximal ends.

Figure 1:
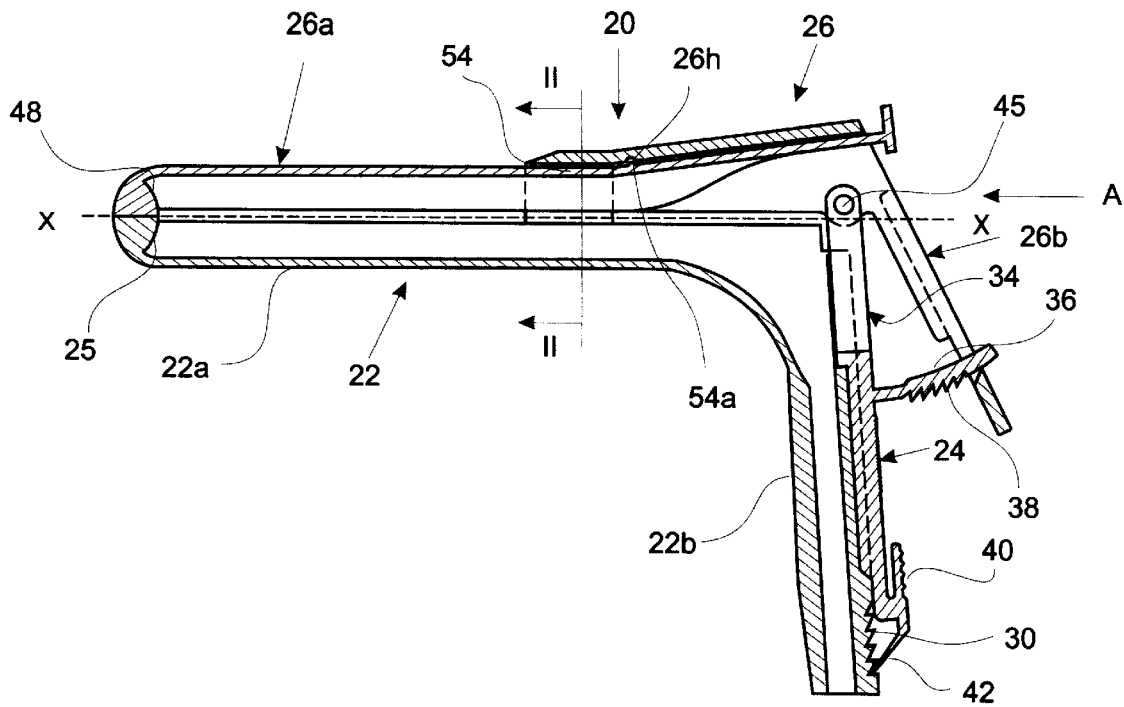
FIG. 1 is a side sectional elevation view of the speculum of the invention.

As can be seen from FIG. 1, which is a side elevation view of the speculum of the invention, the speculum 20 comprises a fixed blade member 22, a slide member 24, and a movable blade member 26.

The fixed blade member 22 has an L-shaped configuration with a blade portion 22a insertable into the patient's vagina, and a handle portion 22b substantially perpendicular to the blade portion 22a. The blade portion 22a is hollow and, as can be seen from FIG. 2, which is a sectional view along line II—II in FIG. 1, it has a semicircular cross-section. The distal end of the blade portion 22a, i.e., the end opposite to the handle portion 22a, has a half-lens 25, which is formed, e.g., molded, integrally with the remaining part of the blade portion 22a. The half-lens 25, in fact, is a portion of a biconvex lens obtained by cutting a lens by half along an optical axis X—X (FIG. 1). FIG. 3 is a view of the vaginal speculum 20 of the invention, which shows the blades of the speculum of FIG. 1 in an open or expanded position.

Ratchet teeth 30 are formed on the lower rear side of the handle portion 22b for the purposes explained later. As shown in FIG. 4, which is a sectional view along line IV—IV in FIG. 3, the part of the handle portion 22a located above the teeth 30 may have a slot 32 of a T-shaped cross-section for guiding a complementary shaped part of the slide member 24, which also has a T-shaped cross-section.

The slide member 24 of the vaginal speculum 20 of the present invention has a fork-like straight portion 34, a rearward projection 36 which is substantially perpendicular to the straight portion 34 and has teeth 38 on one of its sides, and a tail portion 40 with a pawl 42 for engagement with ratchet teeth 30.

Figure 5:
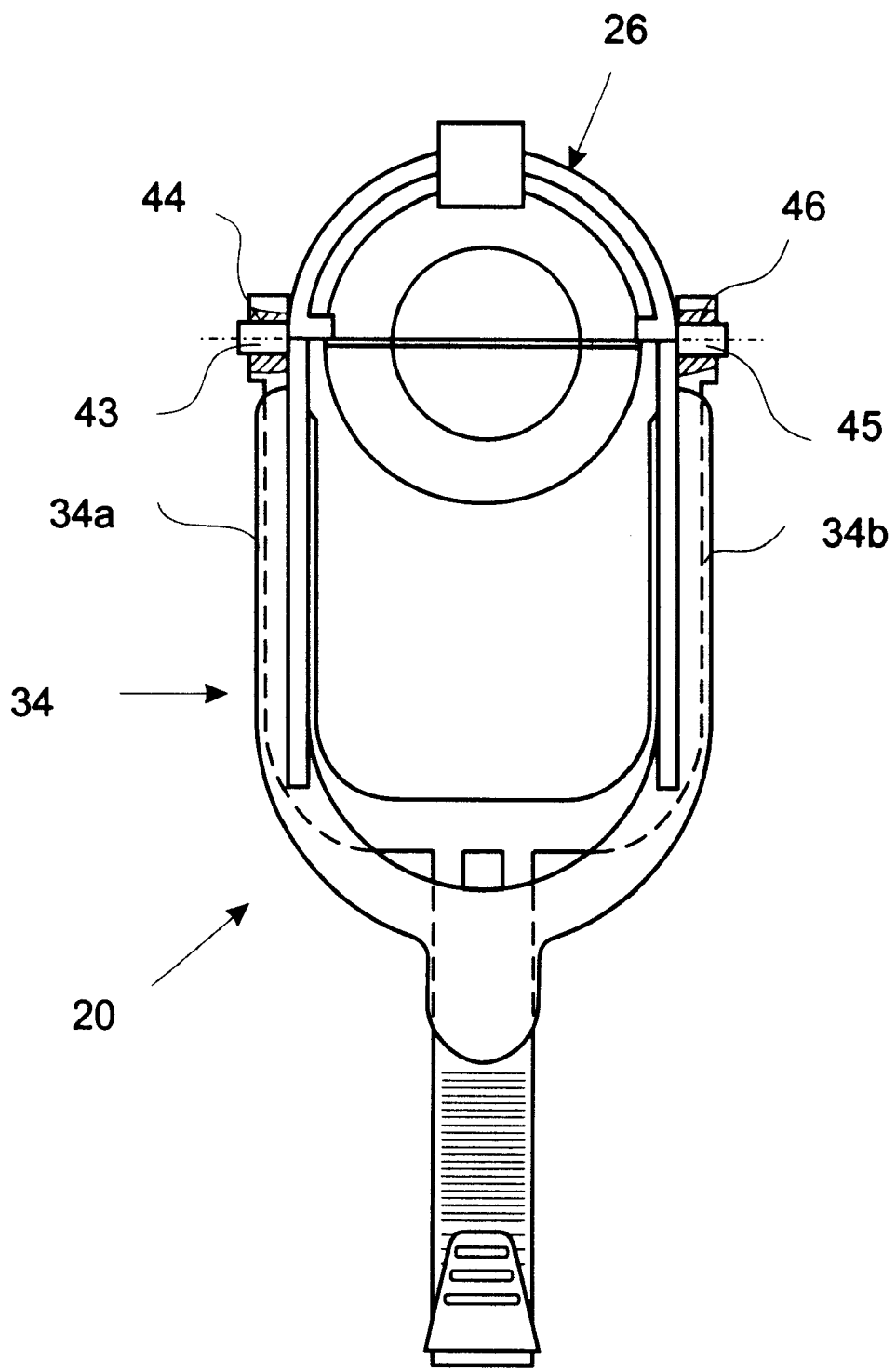
FIG. 5 is a rear view of the vaginal speculum of the invention in the direction of arrow A in FIG. 1.

FIG. 5 is a rear view of the vaginal speculum 20 of the invention in the direction of arrow A in FIG. 1. As can be seen from FIG. 5, the fork-like portion 34 of the slide has holes 44 and 46 on the inner sides of fork legs 34a and 34b. These holes receive projections 43 and 45 formed on the outer side walls of proximal part of the movable member 26. As a result, the movable member 26 can perform rotating or swinging movements around projections 43 and 45 as pivot points.

Similar to the fixed member 22, the movable member 26 has an L-shaped configuration (FIG. 1) with a blade portion 26a insertable into the patient's vagina and a trigger portion 26b formed on the proximal end of the speculum and oriented substantially perpendicular to the blade portion 26a. The insertable blade portion 26a of the moveable member 26 is symmetrical to the insertable blade portion 22a of the fixed member 22 and is complementary thereto so that in a closed state of the speculum 20 shown in FIG. 1 both blade portions form a substantially round cross section. In other words, the blade portion 26 has a semicircular or oval cross-section shown in FIG. 2 and has a half-lens 48 with a flat surface 50 (FIG. 3). Thus, as shown in FIG. 1, in a closed state of the speculum, the blade portions 22 and 26 form a tubular body of a complete round or oval cross-section with a complete biconvex lens formed by two half-lenses 25 and 48 at the distal end of the speculum.

Figure 2:
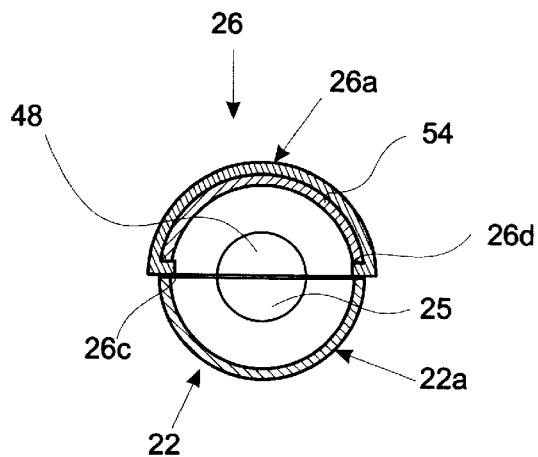
FIG. 2 is a sectional view along line II—II in FIG. 1.
Figures 3, 4:
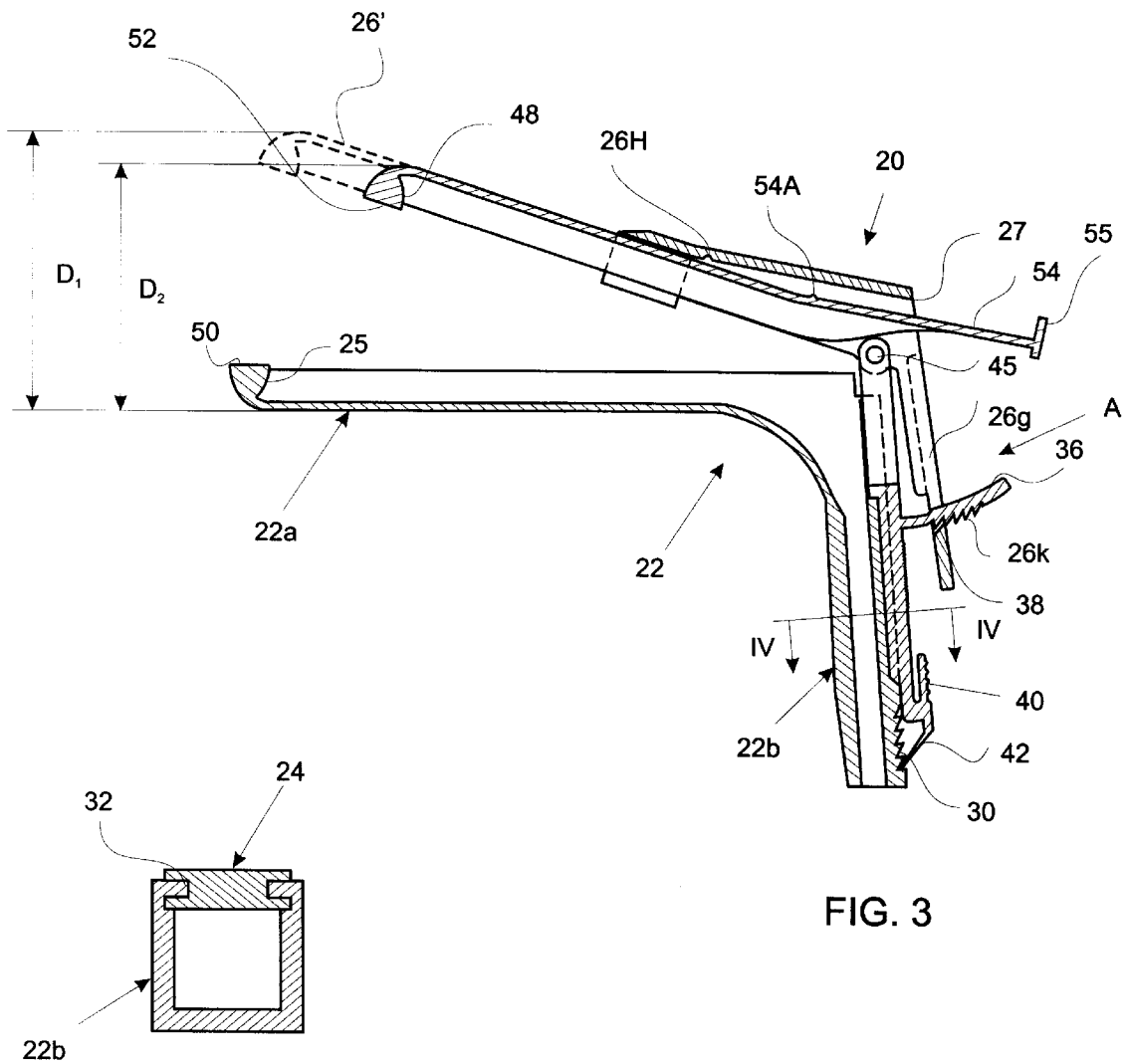
FIG. 3 is a view of the vaginal speculum of FIG. 1, which shows the blades of the speculum in an open or expanded position.
FIG. 4 is a sectional view along line IV—IV in FIG. 3.

As shown in FIG. 2, in the embodiment shown in FIGS. 1 through 5, the movable blade member 26 has, on the inner side, guide edges 26c and 26d, which are bent upward and form guide grooves 26e and 26f. As shown in FIG. 1, guide edges 26c and 26d, may be formed only on a short portion (L) of the entire length of the movable member 26. The grooves 26e and 26f are used for slidingly guiding an adjustable blade 54 (FIGS. 1, 2, and 3) of the moveable member 26. In other words, moveable member 26, in turn, consists of two parts, i.e., the main part 27 with the trigger portion 26b and the adjustable blade 54, which contains the aforementioned insertable part 26a. The adjustable blade 54 may have tight sliding fit in the grooves 26e and 26f r, so that it can be shifted in the rearward direction, i.e., in the direction opposite to the direction of arrow A in FIG. 1, to assume a position shown in FIG. 3. For convenience of shifting, the adjustable blade 54 may have a tab 55 on its rear end. Thus, after the adjustable blade 54 has been shifted in the rearward direction, it will be held in the adjusted position by the aforementioned tight fit. Furthermore, as shown in FIG. 3, in this case the expansion diameter D2 will be smaller than the expansion diameter D1 for non-adjustable blade member 26 shown in FIG. 3 by the broken line 26'.

In order to prevent the adjustable blade 54 from sliding relative to moveable member 26 during insertion of the speculum into the patient's vagina, the proximal end of the adjustable blade 54 has a dent 54a on its outer surface, whereas the moveable portion 26 has an indent 26h on its inner surface for engagement with the dent 54a. Normally the dent 54a is engaged with the indent 26h under the effect of resiliency of the adjustable blade 54, so that during insertion of the distal end of the speculum 20 into the patient's vagina the adjustable blade will not slide relative the moveable portion. In addition, during insertion the tab 55 will bears up against the thumb of a physician who inserts the speculum. In order to adjust the position of the adjustable blade 54 and thus to move it relative to the moveable portion 26, it is necessary to slightly push the proximal end of the adjustable blade 54 down in order to disengage the indent 26h from the dent 54a and then to move the adjustable blade 54a in a required direction.

As shown in FIG. 1, trigger portion 26b has an opening 26g with teeth 26k on the solid part of the trigger 26b for engagement with the teeth 38 on the projection 36 (FIG. 1). The teeth 26k and 38 may be formed as ratchet teeth and a pawl so that pushing on the trigger 26 in the direction of arrow A will rotate the movable member 26 on pivot projections 43 and 45 for expanding the speculum blades 22 and 26. Due to the ratchet engagement between the teeth 26k and 38, after the trigger is releases, the blades 22 and 26 will remain in the expanded position shown in FIG. 3.

The adjustable blade 54 can be completely removed and replaced by another blade having a different length.

If necessary, in addition to the movement of the adjustable blade 54 in the axial direction of the speculum 20, another adjustment can be carried out by guiding the sliding member 24 in guide grooves 32 (FIG. 4), thus raising or lowering the pivot projections 43 and 45 together with the movable member 26 with respect to the fixed member 22. This allows expanding the adjustment range.

Figure 6:
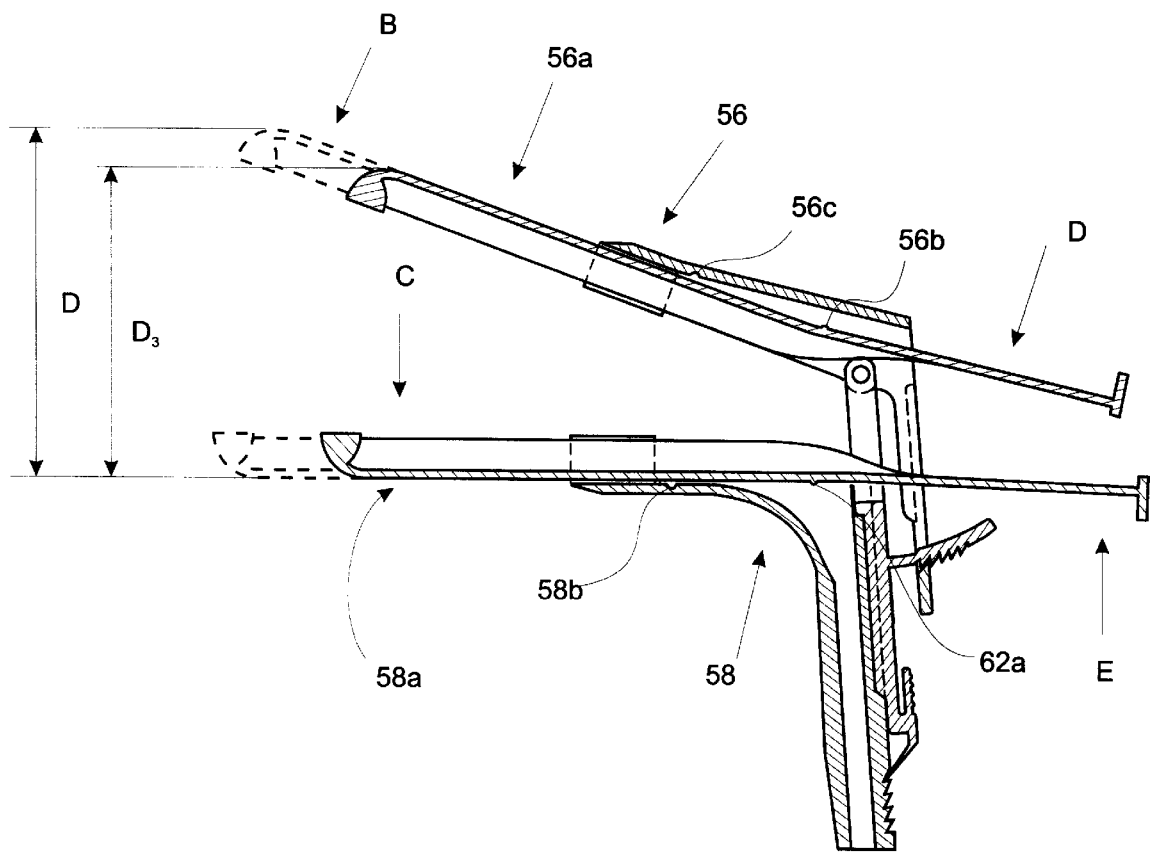
FIG. 6 is a side sectional elevation view of the speculum according to another embodiment of the invention, in which both blades are adjustable.
Figure 7:
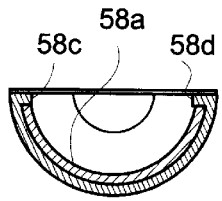
FIG. 7 is a sectional view along line VII—VII in FIG. 6.

FIG. 6 illustrates another embodiment of the vaginal speculum of the invention, in which both blades, i.e., a blade 56a of a movable member 56 and a blade 58a of a fixed member 58 are adjustable. The rest of the construction is the same as in the embodiment shown in FIGS. 1 through 5. As shown in FIG. 7, which is a sectional view along line VII—VII in FIG. 6, the fixed member 58 has on the inner side of the blade portion 58a, guide edges 58c and 58d, which are bent downward and form guide grooves 58e and 58f. As shown in FIG. 6, guide edges 58c and 58d, may be formed only on a short portion ($L_1$) of the entire length of the fixed member 58. The grooves 58e and 58f are used for slidingly guiding the adjustable blade 58a (FIGS. 6) of the fixed member 58. The speculum of FIG. 6 makes it possible to adjust the positions of both adjustable blades 56a and 58a, so that along with the significant decrease in the diameter $D_3$ (FIG. 6), it becomes possible to ensure painless partial withdrawal of the of the blades in an expanded state for observation of the proximal part of the vagina.

In order to prevent the adjustable blade 5 8a from sliding relative to fixed member 58 during insertion of the speculum into the patient's vagina, the proximal end of the adjustable blade 58a has a dent 62a on its outer surface, whereas the fixed member 58 has an indent 58b on its inner surface for engagement with the dent 62a.

The construction of the dent 56b and the indent 56c in the upper adjustable blade 56a and the moveable portion 56 are the same as in the moveable part 26 and in the adjustable blade 54 of the embodiment of FIG. 1.

Figure 8:
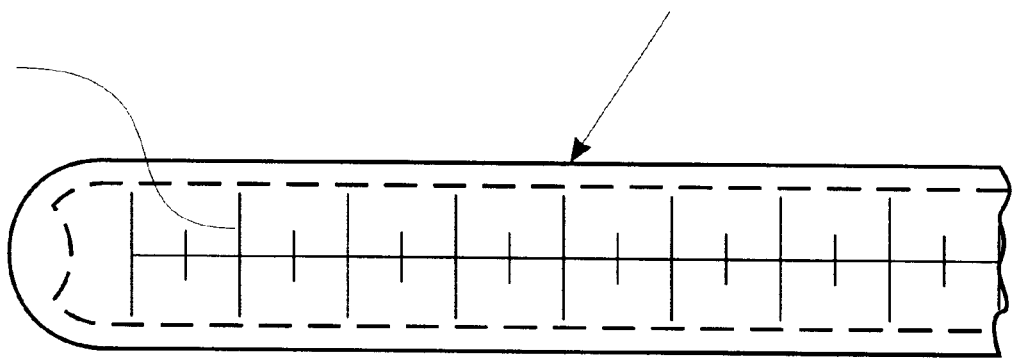
FIG. 8 is a view in the direction of arrow B in FIG. 6.
Figure 9:
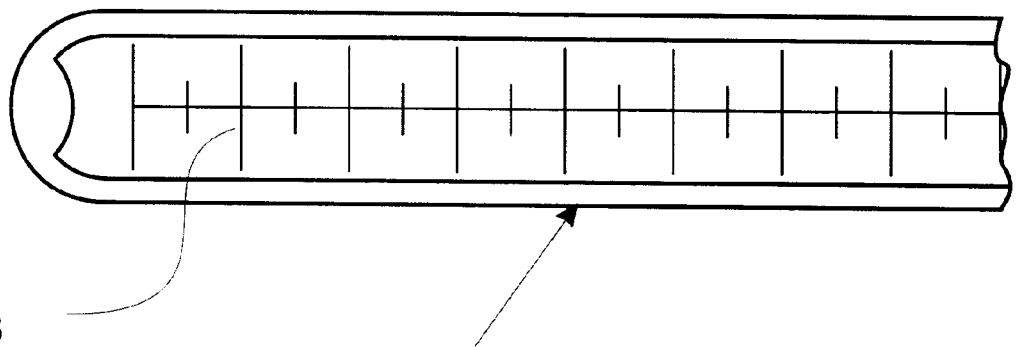
FIG. 9 is a view in the direction of arrow C in FIG. 6.

The vaginal speculum of the present invention is additionally provided with means for locating a position of a vaginal prolapse, of both cystocele-type and rectocele type. For locating a position of the aforementioned prolapses, both adjustable blades have on their proximal ends scales, e.g., in centimeters. FIGS. 8 and 9 are fragmental views in the direction of arrows B and C of FIG. 6, respectively. As can be seen from these drawings, the adjustable blade 56a has a scale 64 with divisions applied onto its outer surface and has the very end as a zero or a reference point with the number in centimeters or inches increased from this point to the proximal end. In other words, the scale 64 can be used as a conventional ruler. Similarly, a scale 68 has divisions applied onto the inner surface of the blade 58a. The divisions should be made black so that they could be seen on the transparent background of the material of the adjustable blades 56a and 58a. The lower scale also has its reference point at the outermost distal point of the adjustable blade 58a.

Figure 10:
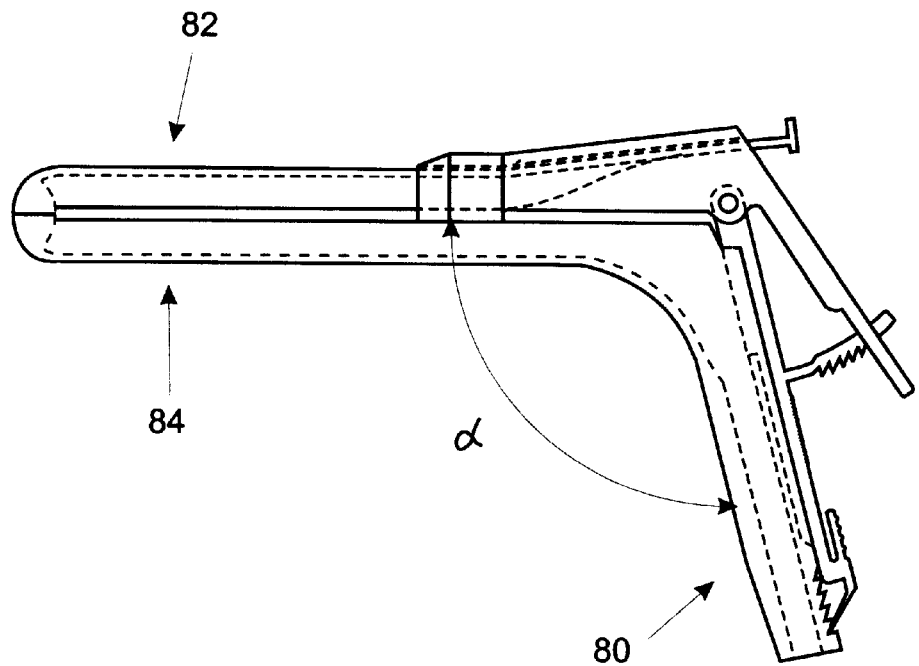
FIG. 10 illustrates another embodiment of the speculum of the invention in which the handle portion is bent backward to form an obtuse angle with the longitudinal direction of the adjustable blades.

FIG. 10 shows another embodiment of the speculum of the invention in which the handle portion 80 can be bent backward to form an obtuse angle $\alpha$ with the longitudinal direction of the adjustable blades 82 and 84 in order not to interfere with outwardly extending parts of the patient's body, such as buttocks, e.g. in overweight women.

Figure 11:
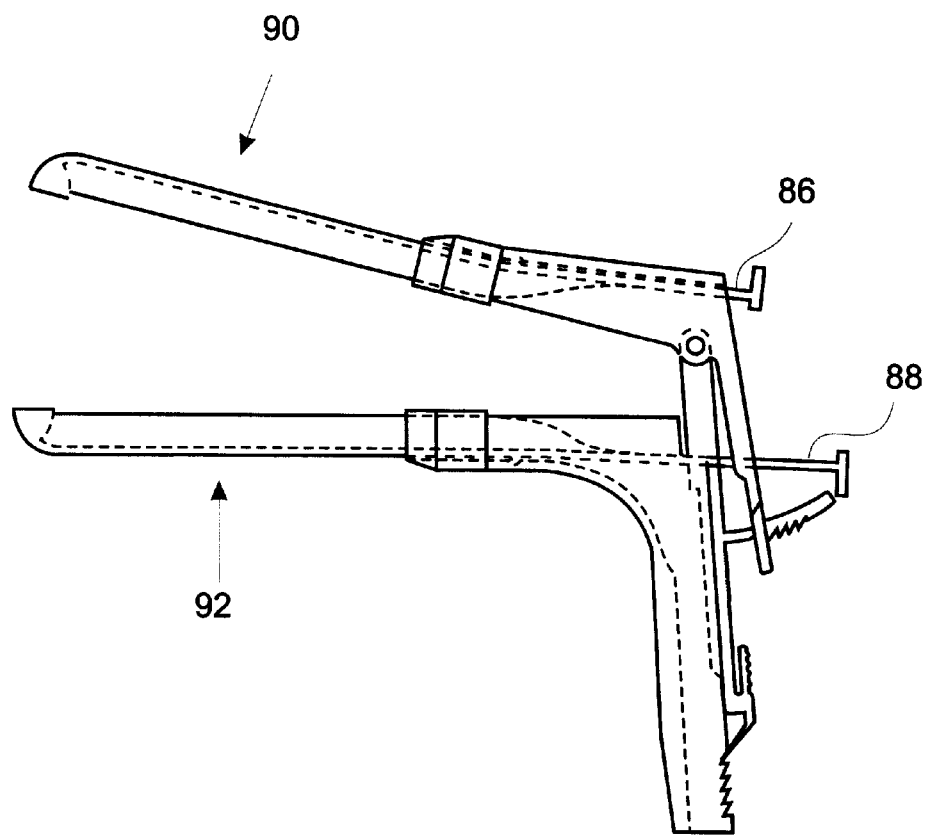
FIG. 11 shows another embodiment of the speculum of the invention in which the proximal ends of the adjustable blades are bent radially outward from the longitudinal axis of the adjustable blades.

FIG. 11 shows another embodiment of the speculum of the invention in which the proximal ends 86 and 88 of the adjustable blades 90 and 92 are bent radially outward from the longitudinal axis of the adjustable blades 90 and 92. This is necessary in order not to obscure the vision through the central opening of the speculum when, during expansion of the distal ends of the blades 90 and 92, their proximal ends 86 and 88 move radially inwardly toward each other.

Figure 12:
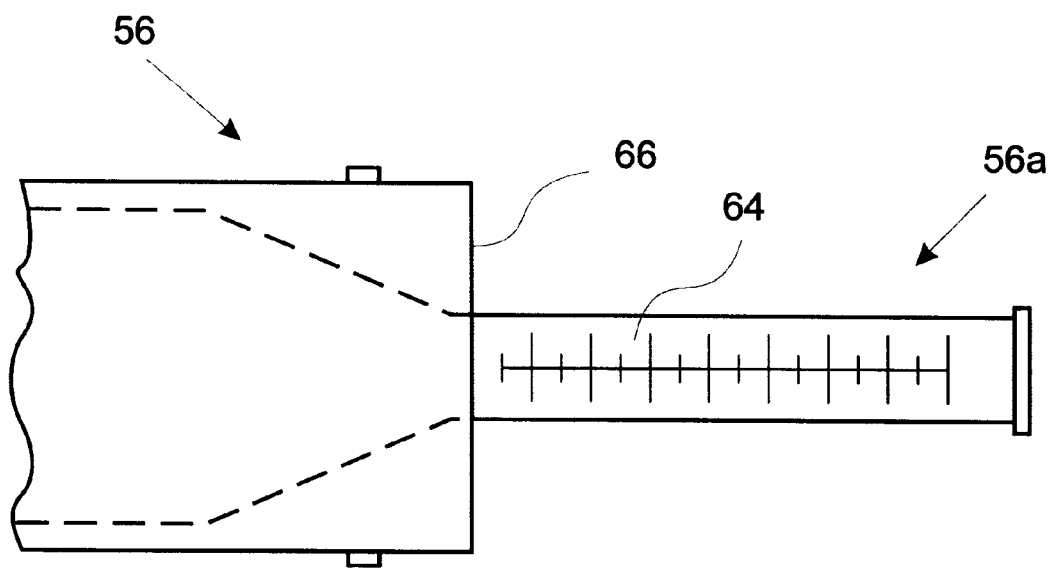
FIGS. 12 and 13 are fragmental views in the direction of arrows D and E of FIG. 6, respectively.
Figure 13:
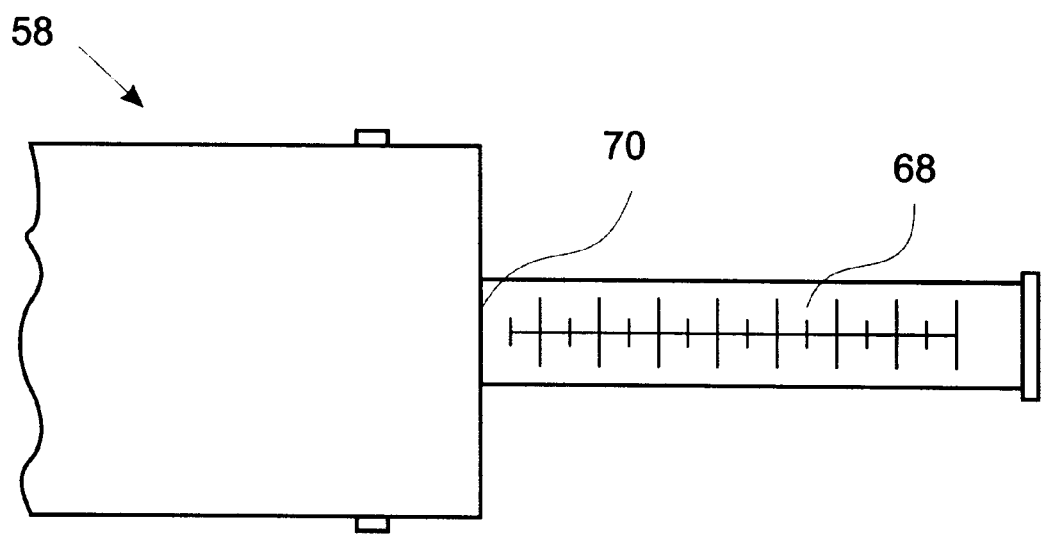

FIGS. 12 and 13 are fragmental views in the direction of arrows D and E of FIG. 6, respectively. As can be seen from these drawings, the scale 64 on the movable or adjustable blade 56a may extend further to the protruding proximal end 60 of the adjustable blade 56a, so that measurements can be read with regard to the rear edge 66 of the movable part 56. The same principle can applied to the fixed member 58, where divisions of the scale 68 can extend to the protruding proximal end 72 (FIG. 13), so that measurements can be read with regard to the rear edge 70 of the fixed member 58.

Procedure for the use of the retractable vaginal speculum

The procedure is started from inspection of the vaginal introitus to determine the status of the vaginal skin, the size of the vaginal outlet, and the presence or absence of pelvic organ prolapse. A retractable vaginal speculum of a required size is then chosen.

Since a retractable vaginal speculum is normally a disposable instrument, which is sterilized and packed into a sealed package, it is unpacked and removed from the package. In the case of the speculum of FIGS. 1 through 5, the insertable ends 26a and 22a of the blade members 22 and 26 are then lubricated using a water-soluble lubricant. The insertable ends 26a and 22a of the speculum 20, are then gently inserted into the vaginal canal in a closed state of the speculum 20 shown in FIG. 1, and are advanced all the way to the vaginal vault or at the level of the uterine cervix 101, shown in FIG. 14, which is a sectional view of normal reproductive organs of a woman.

The physician first visually observes the condition of the uterus cervix through the optical lens formed by semilenses 48 and 25. The purpose of this observation is to detect initial changes on the cervix that could not be detected by a naked eye. Such changes may be initial erosion, papilomas, etc.

The speculum 20 is then opened by moving the blade members 22 and 26 apart to further visualize the vaginal vault or the cervix. This is done by pushing on the trigger portion 26b so that the teeth 26k slide in a ratchet manner over the teeth 38 of the projection 36. As a result, the blade members 22 and 26 of the speculum assume the positions shown in FIG. 3 and thus expand the vaginal cavity (not shown in the drawings).

The physician can then observe the appearance of the vaginal mucosa at the level of the vault, or observe the appearance of the cervix. If necessary, the length of the vaginal canal is measured from the vaginal vault or the posterior aspect of the cervico-vaginal junction to the level of the hymenal line. This is achieved by pushing down on the tab 55 of the adjustable blade 54 for disengaging the dent 54a from the indent 26h and by moving the adjustable blade 54 to a required position. Measurement is made by reading the numbers of the scale 64 with regard to the hymeneal line, as will be described later. As shown in FIGS. 8 and 9, where FIG. 8 is a view in the direction of arrow B, and FIG. 9 is a view in the direction of arrow C in FIG. 6, the divisions of the scale are applied onto the entire length of the blades 54 and 25 in the embodiment of FIG. 1, and of the blades 54a and 58a in the embodiment of FIG. 6, so that the physician could measure the distance from the hymeneal ring to the cervix, as well as the distance to the end of the prolapse using the very end of the distal end as the reference point for measurement. If necessary, the physician performs paps smear and/or collection of fluids for culture and or cytology as indicated. Slight thickening of the curved end walls on the distal ends of the blades 20 and 22 caused by the formation of semilenses does not create any obstacles for this operation.

For separate observation of the condition of one of the walls of the vagina, the adjustable blade, e.g. blade 54 (FIGS. 1 and 2) is then retracted halfway so that the blade of the speculum 20 (or speculum 56) is in a position required for the observation of the exposed wall. Since one of the blades, i.e., the blade 22 remain in the initial position (FIG. 3) and another blade, i.e., 26, is partially withdrawn, the physician may observe the condition of the exposed part of the vagina wall for observation and thus to see prolapses on the exposed wall. This would be unattainable for the conventional speculum without completely withdrawing the entire speculum, disassembling it, and using only one part as a spade for pressing on one wall of the vagina in order to expose the opposite wall for observation. In the case of the embodiment of FIG. 6, both adjustable blades 56a and 58a can be withdrawn in alternating sequence, or can be retracted both together to see if the uterus or the vaginal vault (dome) will drop further down. The degree of the drop of the uterus or the vaginal vault (dome)(if the uterus is gone) in relation to the hymeneal line can be measured with the calibrated retractable blade. This is easily done by positioning the tip of the sliding blade to the lowest edge of the prolapsing organ, i.e. cervix or vaginal vault or cystocele or rectocele and measuring from that distance to the level of the hymeneal line.

Figure 14:
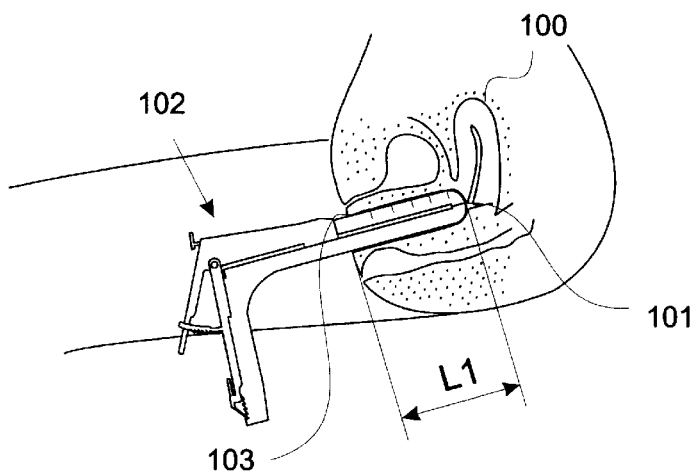
FIG. 14 is a sectional view of normal reproductive organs of a woman.
Figure 15:
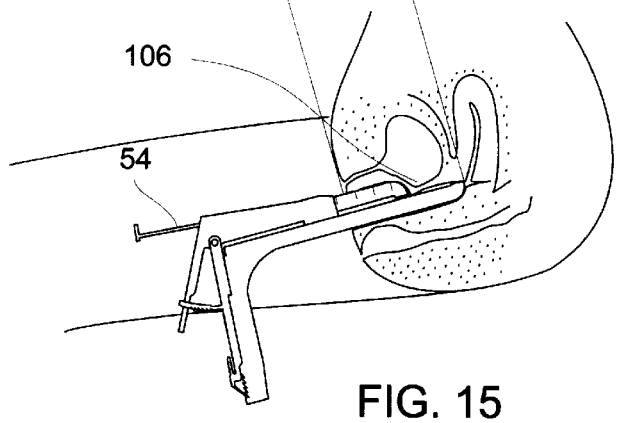
FIG. 15 shows an example of cystocele inside the vaginal canal.
Figure 16:
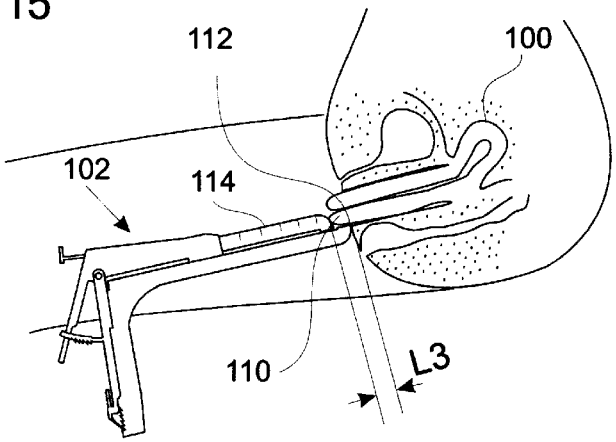
FIG. 16 shows a condition of a cystocele protruding outside the vagina.

The aforementioned measuring procedure will be now explained with reference to FIGS. 14, 15, and 16; wherein FIG. 12 shows a normal anatomy of female reproductive organs, FIG. 15 shows an example of cystocele inside the vaginal canal and method for measuring its position and dimensions, and FIG. 16 shows a condition of a cystocele protruding outside the vagina and a method for measuring the length of this cystocele.

As shown in FIG. 14, the distance L between the tip of the cervix 100 and the hymeneal ring is measured by inserting the speculum 102 in a closed state shown in FIG. 1 to contact with the dome of the uterus 100 and by reading the number on the scales of the blades at the hymeneal line 104. The distance between these two points will be in centimeters and will be recorded as a minus number. For example, if the cervix is prolapsing (not shown) and the distance between the edge of the cervix inside the vaginal canal to the hymeneal ring is 3 centimeters, then the cervix prolapse is −3 cm. Likewise, if, as shown in FIG. 15, there is a cystocele 106 and it is prolapsing or dropping, the physician can retract the adjustable blade 54 (FIG. 3), or the adjustable blade 56a (FIG. 6), and then move it to contact of the distal tip of this adjustable blade with the edge of the systole. The distance L1 between with the edge of the cystocele 106, touching the tip of the retractable blade 106, and the level of the hymeneal line 108 is then measured with regard to the hymeneal line 104 as a reference point. If L1 is 4 centimeters, then the prolapsing cystocele is −4 cm. The same procedure can be performed with regard to rectocele (not shown) by moving the adjustable blade 58a (FIG. 6).

If the prolapse is so severe that, as shown in FIG. 16, it is coming out of the vaginal opening which can be observed even before the speculum is inserted or after the speculum is completely removed and the organ prolapsing; for example, the cystocele 110 is protruding out, then the measurement of the prolapse will be a distance L2 from the hymeneal line 112 to the furthest tip of the prolapsing cystocele. This distance is measured by means of the scale on the tip 114 of the speculum 116 as by a conventional ruler. If the prolapse is dropping outside the hymeneal line; i.e. is 5 centimeters, the cystocele prolapse is +5 cm.

In accordance with an alternative method, the severity and positions of the prolapses can be measured by using rear edges 66 (FIG. 12) and 70 (FIG. 13) of respective proximal portions of the blades. In this case, the distance L1 can be measured by reading the number on the scale 68 between the edge 70 of the cystocele 106 touching the tip of the retractable blade 106 and between the edge 70 and the hymeneal line 108. The length L1 will be determined by subtracting the second reading from the first one. The same is applicable for measuring rectocele (not shown).

What is claimed is:

1. A vaginal speculum comprising:
   a first member having a proximal part and a distal part which has an elongated configuration and is insertable into a women's vagina;
   a second member having a proximal part and a distal part which has an elongated configuration and is insertable into a women's vagina;
   a third member moveable together with said first member with respect to said second member in a direction transverse to said elongated configuration and having means for fixing said third member to said second member in a selected position with respect thereto, said third member having means for pivotally supporting said first member with respect to said second member for expanding said speculum from a closed state in which said first member and said second member are in contact with each other and have a closed cross-sectional configuration and an expanded state in which said first member and said second member are moved apart in said direction transverse to said elongated configuration;
   means for fixing said second member with respect to said first member in said expanded state;
   at least one of said first and said second members having its respective distal part movable with respect to said proximal part in the direction of said elongated configuration thus forming at least one movable blade.

2. The vaginal speculum of claim 1, wherein said at least one of said first and said second members has on its respective proximal part guide means for guiding said at least one movable blade.

3. The vaginal speculum of claim 2, wherein at least one of said first and said second members having a measurement scale at least on a part of said at least one movable blade.

4. The vaginal speculum of claim 3, wherein said scale has its reference point at the distal tip of said at least one movable blade.

5. The vaginal speculum of claim 1, having means for fixing said at least one movable blade with respect to said proximal part.

6. the vaginal speculum of claim 3, having means for fixing said at least one movable blade with respect to said proximal part.

7. The vaginal speculum of claim 4 having means for fixing said at least one movable blade with respect to said proximal part.

8. The vaginal speculum of claim 1, wherein said first member and said second member are made of a transparent material, said first member having on its distal end a first half-lens, said second member having on its distal tip a second half-lens, said first and said second half lenses forming in said closed state a complete optical lens.

9. The vaginal speculum of claim 8, wherein said optical lens is a bifocal lens.

10. The vaginal speculum of claim 3, wherein said first member and said second member are made of a transparent material, said first member having on its distal tip a first half-lens, said second member having on its distal tip a second half-lens, said first and said second half lenses forming in said closed state a complete optical lens.

11. The vaginal speculum of claim 10, wherein said optical lens is a bifocal lens.

12. The vaginal speculum of claim 4, wherein said first member and said second member are made of a transparent material, said first member having on its distal tip a first half-lens, said second member having on its distal tip a second half-lens, said first and said second half lenses forming in said closed state a complete optical lens.

13. The vaginal speculum of claim 12, wherein said optical lens is a bifocal lens.

14. The vaginal speculum of claim 5, wherein said first member and said second member are made of a transparent material, said first member having on its distal tip a first half-lens, said second member having on its distal tip a second half-lens, said first and said second half lenses forming in said closed state a complete optical lens.

15. The vaginal speculum of claim 14, wherein said optical lens is a bifocal lens.

16. The vaginal speculum of claim 6, wherein said first member and said second member are made of a transparent material, said first member having on its distal tip a first half-lens, said second member having on its distal tip a second half-lens, said first and said second half lenses forming in said closed state a complete optical lens.

17. The vaginal speculum of claim 16, wherein said optical lens is a bifocal lens.

18. The vaginal speculum of claim 1, wherein said means for fixing said third member to said second member in a selected position comprise a guide slot in said proximal part of said second member for guiding said third member in said direction transverse to said elongated configuration, first ratchet teeth on said distal part of said second member and a first pawl that engages said first ratchet teeth.

19. The vaginal speculum of claim 1, wherein said means for fixing said second member with respect to said first member in said expanded state comprise second ratchet teeth on said third member and a second pawl on said first member for engaging said second ratchet teeth.

20. The vaginal speculum of claim 2, wherein said means for fixing said third member to said second member in a selected position comprise a guide slot in said distal part of said second member for guiding said third member in said direction transverse to said elongated configuration, first ratchet teeth on said distal part of said second member, and a first pawl that engages said first ratchet teeth; said means for fixing said second member with respect to said first member in said expanded state comprising second ratchet teeth on said third member and a second pawl on said first member for engaging said second ratchet teeth.

21. The vaginal speculum of claim 3, wherein said means for fixing said third member to said second member in a selected position comprise a guide slot in said distal part of said second member for guiding said third member in said direction transverse to said elongated configuration, first ratchet teeth on said distal part of said second member, and a first pawl that engages said first ratchet teeth; said means for fixing said second member with respect to said first member in said expanded state comprising second ratchet teeth on said third member and a second pawl on said first member for engaging said second ratchet teeth.

22. The vaginal speculum of claim 4, wherein said means for fixing said third member to said second member in a selected position comprise a guide slot in said distal part of said second member for guiding said third member in said direction transverse to said elongated configuration, first ratchet teeth on said distal part of said second member, and a first pawl that engages said first ratchet teeth; said means for fixing said second member with respect to said first member in said expanded state comprising second ratchet teeth on said third member and a second pawl on said first member for engaging said second ratchet teeth.

23. The vaginal speculum of claim 5, wherein said means for fixing said third member to said second member in a selected position comprise a guide slot in said distal part of said second member for guiding said third member in said direction transverse to said elongated configuration, first ratchet teeth on said distal part of said second member, and a first pawl that engages said first ratchet teeth; said means for fixing said second member with respect to said first member in said expanded state comprising second ratchet teeth on said third member and a second pawl on said first member for engaging said second ratchet teeth.

24. A vaginal speculum having a longitudinal direction and blades extending in said longitudinal direction, said speculum comprising:

a first member having a first proximal part fixed against movements in said longitudinal direction and located outside the vagina during the use of said speculum and a distal part moveable in said longitudinal direction and insertable into vagina during the use of said speculum said distal part comprises a first moveable blade slidingly guided with a tight sliding fit in said first proximal part in said longitudinal;

a second member having a second proximal part fixed against movement movements in said longitudinal direction and located outside the vagina during the use of said speculum and a distal part moveable in said longitudinal direction and insertable into vagina during the use of said speculum, said distal part comprising a second moveable blade slidingly guided with a tight sliding fit in said second proximal part in said longitudinal direction;

a third member moveable together with said first member with respect to said second member in a direction transverse to said longitudinal direction and having means for fixing said third member to said second member in a selected position with respect thereto, said third member having means for pivotally supporting said first member with respect to said second member for expanding said speculum from a closed state in which said first member and said second member are in contact with each other and have a closed cross-sectional configuration and an expanded state in which said first member and said second member are moved apart in said direction transverse to said longitudinal direction;

means for fixing said second member with respect to said first member in said expanded state.

25. The vaginal speculum of claim 24, wherein said first moveable blade and said second moveable blade are completely removable from said first proximal part and said second proximal part, respectively.

26. The vaginal speculum of claim 24, wherein said proximal parts of said first and said second members have means for guiding said first and said second moveable blades, respectively.

27. The vaginal speculum of claim 24, wherein said first and said second moveable blades each has a measurement scale at least on a part of its lengths.

28. The vaginal speculum of claim 26, wherein said scale has its reference point at the distal tip of said respective movable blade.

29. The vaginal speculum of claim 26, having means for fixing said first and said second moveable blades with respect to their respective proximal parts.

30. The vaginal speculum of claim 24, wherein at least said first moveable blade and said second moveable blade are made of a transparent material, said first moveable blade having on its distal tip a first half-lens, said second moveable blade having on its distal tip a second half-lens, said first and said second half lenses forming in said closed state a complete optical lens.

31. The vaginal speculum of claim 27, wherein said optical lens is a bifocal lens.

* * * * *